United States Patent [19]
Kanno et al.

[11] 4,307,097
[45] Dec. 22, 1981

[54] METHOD OF REDUCING INCREASED INTRACRANIAL PRESSURE

[75] Inventors: Takeshi Kanno; Mitsunori Gaino, both of Omiya; Kenichi Yoshimoto, Nishinomiya; Keiichi Shintomi, Suita, all of Japan

[73] Assignee: Tanabe Seiyaku Co., Ltd., Osaka, Japan

[21] Appl. No.: 213,946

[22] Filed: Dec. 8, 1980

[30] Foreign Application Priority Data

Dec. 28, 1979 [JP] Japan .................... 54-173823

[51] Int. Cl.³ .................... A61K 31/495
[52] U.S. Cl. .................... 424/250
[58] Field of Search .................... 424/250

[56] References Cited
U.S. PATENT DOCUMENTS
3,951,983  4/1976  Danilewicz et al. .......... 424/250 X FOREIGN PATENT DOCUMENTS
53-21127  7/1978  Japan .

OTHER PUBLICATIONS
Derwent No. 27561 A/15 Tanabe Pharm. KK.
Merck Index, 9th Ed., 1976, entry 5575.
Merck Index, 9th Ed., 1976, entry 8343.
Merck Index, 9th Ed., 1976, entry 8497.

Primary Examiner—Frank Cacciapaglia, Jr.
Attorney, Agent, or Firm—Bierman & Bierman

[57] ABSTRACT

Increased intracranial pressure in warm-blooded animals is reduced by administering to the warm-blooded animals a therapeutically effective amount of a propanol derivative of the formula:

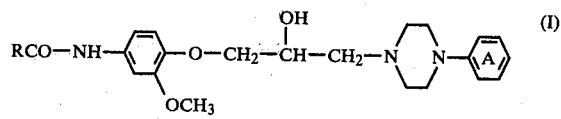

wherein R is alkyl having one to 4 carbon atoms and Ring A is phenyl, halogenophenyl, methylphenyl or trifluoromethylphenyl, or a pharmaceutically acceptable acid addition salt thereof.

11 Claims, No Drawings

METHOD OF REDUCING INCREASED INTRACRANIAL PRESSURE

This invention relates to a method of reducing increased intracranial pressure in a warm-blooded animal through administering to said warm-blooded animal an effective amount of a propanol derivative of the formula:

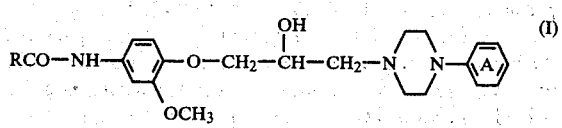

wherein R is alkyl having one to 4 carbon atoms and Ring A is phenyl, halogenophenyl, methylphenyl or trifluoromethylphenyl, or a pharmaceutically acceptable acid addition salt thereof.

Cerebral edema, which is a well-known complication of various cerebral diseases (e.g., cerebral hemorrhage, subarachnoid hemorrhage, cerebral thrombosis, cerebral embolism, head injury, cerebral tumor and encephalomyelitis), induces an increase in intracranial pressure due to compression of neighbouring brain tissues. Moreover, such increased intracranial pressure is known to adversely affect cerebral metabolism, result in disturbances of cerebral circulation and further aggravate cerebral edema. Therefore, the increased intracranial pressure exerts serious adverse effects on patients or is sometimes fatal to them. In this respect, a hypertonic solution (1000–1500 milliosmols/kg.$H_2O$) of glycerol or mannitol has been used for therapeutic treatment of patients suffering from increased intracranial pressure. The intravenous infusion of the hypertonic solution raises blood osmolality and creates an osmotic gradient between plasma and brain with resultant net removal of water from brain. Thus, the therapeutic effect of the hypertonic solution on the increased intracranial pressure is based on the hyperosmolar dehydrating effect and therefore, in order to obtain the desired therapeutic effect, as much as 500 to 1,500 ml/man/day of the hypertonic solution must be administered to patients. Such hypertonic solution is also disadvantageous in that its intravenous infusion often causes haematological abnormalities (e.g., disturbance of water-electrolyte equilibrium, haemolysis, decrease in haematocrit level) and is followed by a rebound increase in the intracranial pressure to levels higher than those that existed before therapy.

An object of the present invention is to provide a method of reducing or treating increased intracranial pressure in a warm-blooded animal (including man) in need of such treatment by administering to the warm-blooded animal a therapeutically effective amount of the propanol derivative (I) or a pharmaceutically acceptable acid addition salt thereof. Another object of the invention is to provide a method of reducing or decreasing the increased intracranial pressure in the warm-blooded animal without haematological abnormalities, rebound increase in said pressure and other untoward side effects as seen in the hypertonic solution of glycerol or mannitol. Other object of the invention is to provide a method of treating a warm-blooded animal suffering from a disease or condition attributable to increased intracranial pressure. Still other object is to provide a pharmaceutical composition, useful for reducing or treating increased intracranial pressure, comprising a therapeutically effective amount of the propanol derivative (I) or a salt thereof and a pharmaceutically acceptable carrier therefor. Further objects of the present invention will be apparent from the following description and claims.

The propanol derivative (I) of the present invention shows a significant decrease in the intracranial pressure at a remarkably low dose such as 0.1–2 mg/kg of body weight/day.

Representative examples of such compound include those of the formula (I) in which R is alkyl having one to 4 carbon atoms (e.g., methyl, ethyl, propyl, butyl), and Ring A is phenyl, methylphenyl (e.g., 2-methylphenyl), chlorophenyl (e.g., 2-chlorophenyl, 3-chlorophenyl, 4-chlorophenyl), fluorophenyl (e.g., 2-fluorophenyl, 3-fluorophenyl, 4-fluorophenyl) or trifluoromethylphenyl (e.g., 3-trifluoromethylphenyl). Among those compounds, preferred group of compounds are those of the formula (I) in which R is methyl and Ring A is phenyl, chlorophenyl or fluorophenyl. A more preferred group of compounds are those of the formula (I) in which R is methyl and Ring A is phenyl, 2-chlorophenyl, 2-fluorophenyl or 3-fluorophenyl; and the most preferred compound is 1-(4-acetamido-2-methoxyphenoxy)-3-[4-(3-fluorophenyl)piperazino]-2-propanol. All of these propanol derivatives (I) and the synthesize thereof have already been disclosed in Japanese Patent Publication (unexamined) No. 21127/1978.

The method of the present invention is applicable to the therapeutic treatment or prognosis of a warm-blooded animal, including man, suffering from increased intracranial pressure due to various cerebral diseases such as cerebral infarction, cerebral thrombosis, cerebral embolism, cerebral hemorrhage, subarachnoid hemorrhage, head injury, cerebral tumor, cerebral edema, encephalomyelitis and the like. The propanol derivative (I) may be also used to ameliorate such various cerebral diseases as mentioned above. Moreover, since the propanol derivative (I) has a potent cerebral blood flow-increasing activity in addition to its effect on the intracranial pressure, it can be used to improve the cerebral circulation, especially in ischemic areas in brain.

According to the present invention, the propanol derivative (I) may be employed either as the free base or in the form of a pharmaceutically acceptable acid addition salt thereof. Pharmaceutically acceptable acid addition salts of the propanol derivative (I) include, for example, inorganic acid addition salts such as hydrochloride, phosphate, nitrate and sulfate; and organic acid addition salts such as acetate, lactate, citrate, fumarate, maleate, glycinate, aspartate, methanesulfonate and benzoate. The propanol derivative (I) or a pharmaceutically acceptable acid addition salt thereof can be administered either orally or parenterally (e.g., intravenously, intramuscularly, or subcutaneously). The therapeutic dose of the propanol derivative (I) or its salt depends on route of administration; the conditions of diseases; and the particular diseases to be treated. In general, it may be used at a dose of about 0.05 to about 50 mg (in terms of free base) per kilogram of body weight per day. When administered parenterally (e.g., intravenously), it is especially preferred to use about 0.1 to about 5 mg (in terms of free base) per kilogram of body weight per day. On the other hand, the preferred dose of the propanol derivative (I) or its salt for use by oral administration is about 1 to about 10 mg (in terms of free base) per kilogram of body weight per day. In the present invention, the propanol derivative (I) and its salt are used in the form of a pharmaceutical preparation containing the same derivative in conjunction or admixture with a pharmaceutical excipient suitable for oral or parenteral administration. Suitable excipients include, for example, lactose, mannitol, starch, crystalline cellulose, calcium citrate, calcium phosphate, gelatine, dextrin, methylcellulose, sodium carboxymethylcellulose, hydroxypropylcellulose, polyvinylpyrrolidone, stearic acid, magnesium stearate, calcium stearate, talcum and other known medicinal excipients. When administered orally, the pharmaceutical preparations may be in solid form such as tablets, pills, powders, capsules or granules; or in liquid form such as solutions or suspensions. On the other hand, when administered parenterally, the pharmaceutical preparations may be preferably employed in the form of injections. An injection for intravenous drip infusion is especially suitable for parenteral administration. Preferred examples of the injection include aqueous solutions comprising the propanol derivative (I) or its salt and at least one member selected from mannitol, sorbitol, glycerol, xylitol, fructose, maltose and sodium chloride. Suitable concentration of the propanol derivative (I) or its salt in the aqueous solution is about 0.0004 to about 1.5 w/v %, especially about 0.005 to about 0.8 w/v %. It is preferred that said aqueous solution of the present invention for parenteral administration has an osmotic pressure approximately not lower than that of blood plasma. Therefore, mannitol, sorbitol, glycerol, xylitol, fructose, maltose or sodium chloride should be used in an amount sufficient to adjust the osmotic pressure of the aqueous solution to a level not lower than about 250 milliosmols/kg.$H_2O$, especially about 270 to about 850 milliosmols/kg.$H_2O$, and more especially about 270 to about 550 milliosmols/kg.$H_2O$. For this purpose, mannitol, sorbitol, xylitol or fructose must be used in an amount of at least about 4.6 w/v %, glycerol in an amount of at least about 2.3 w/v %, maltose in an amount of at least about 9.3 w/v % or sodium chloride in an amount of at least about 0.8 w/v %. About 5 to about 15 w/v % of mannitol, sorbitol, xylitol or fructose, about 2.5 to about 7.5 w/v % of glycerol, about 10 to about 30 w/v % of maltose and about 0.9 to about 2.7 w/v % of sodium chloride may be used to adjust the osmotic pressure of said aqueous solution to a level of about 270 to about 850 milliosmols/kg.$H_2O$. On the other hand, about 5 to about 10 w/v % of mannitol, sorbitol, xylitol or fructose, about 2.5 to about 5 w/v % of glycerol, about 10 to about 20 w/v % of maltose and about 0.9 to about 1.8 w/v % of sodium chloride may be used to adjust the osmotic pressure of said aqueous solution to a level of about 270 to about 550 milliosmols/kg.$H_2O$. Such aqueous solution for injection may be formulated by dissolving the propanol derivative (I) or a salt thereof in an aqueous solution containing at least one member selected from mannitol, sorbitol, glycerol, xylitol, fructose, maltose and sodium chloride. It is preferred to adjust a pH of the aqueous solution to about 4 to about 7.5, and conventional alkaline agents such as sodium hydroxide are preferably employed to adjust the pH of said solution. Further, said aqueous solution may be sterilized or filtered in a conventional manner. If desired, to said aqueous solution may be added other drugs or carriers suitable for use in injection.

The propanol derivative (I) shows significant decrease in intracranial pressure even when administered at such a remarkably low dose as 0.5 mg/kg of body weight; said therapeutic effect lasts for a long period of time; e.g. for more than 5-6 hours; and its use is not associated with rebound increase in intracranial pressure. Unlike the hypertonic solutions of glycerol or mannitol, the therapeutic effect of the propanol derivative (I) of the present invention is not ascribable to the cerebral dehydrating effect and, therefore, said derivative (I) can be used either orally or parenterally. The propanol derivative (I) may also be used for the treatment of prophylaxis of increased intracranial pressure during and after brain surgical operation. Moreover, the propanol derivative (I) may be used for improving impaired consciousness, nervous disturbance and subjective symptoms (e.g., headache, nausea, vomiting) which are attributed to the cerebral diseases such as those mentioned hereinbefore. Further, whereas it is known that cerebral edema induces a rise in intracranial pressure and increased intracranial pressure serves to cause a build-up of edema which in turn impairs cerebral circulation, the propanol derivative (I) can interrupt this vicious cycle of cerebral diseases because of its potent intracranial pressure-lowering effect and its ability to ameliorate the cerebral circulatory impairment. The toxicity of the propanol derivative (I) of the present invention is low. For example, when a therapeutic index is estimated in terms of the ratio of the 50% lethal dose to the minimum effective dose (i.e., a minimum dose at which a test compound shows intracranial pressure-lowering activity), 1-(4-acetamido-2-methoxyphenoxy)-3-[4-(3-fluorophenyl)piperazino[-2-propanol of the invention when administered orally or intravenously shows the therapeutic index of not less than about 400.

Concomitantly, the propanol derivative (I) of the present invention is prepared in accordance with the method described in Japanese Patent Publication (unexamined) No. 21127/1978, i.e., by reacting a 3-(4-acylamino-2-methoxyphenoxy)-1,2-epoxypropane with a piperazine derivative of the formula:

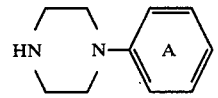

wherein Ring A is the same as defined above.

EXAMPLE 1

(Effect of i.v. injection of test compounds on intracranial pressure in rats)

Method

Male SD-strain rats weighing 500 to 800 g (each group consisting of 5 rats) were anesthetized with urethane. A solution of a test compound in an aqueous 5 w/v % mannitol solution was infused via the femoral vein at a rate of 0.2 ml/kg/minute for 40 minutes (when the test compound was used in the form of free base, said solution was prepared by dissolving it in an aqueous 5 w/v % mannitol solution with the aid of 0.5 N hydrochloric acid). Intracranial pressure (i.e., cerebrospinal fluid pressure in the cisterna magna) was continuously monitored via a cannula inserted in the cisterna magna. The cannula was connected to a transducer, and recordings were made on graph paper. The effect of the test compound on the intracranial pressure was estimated in terms of the increase or decrease in intracranial pressure, which was calculated in accordance with the following formula:

Changes (%) in intracranial pressure =

$$\left[\frac{\text{Intracranial pressure (mm H}_2\text{O)}\text{ measured after administration of test compound}}{\text{Intracranial pressure (mm H}_2\text{O)}\text{ measured before administration of test compound}}\right] \times 100$$

Test compounds 1. 1-(4-acetamido-2-methoxyphenoxy)-3-(4-phenylpiperazino)-2-propanol
2. 1-(4-acetamido-2-methoxyphenoxy)-3-[4-(2-methylphenyl)piperazino]-2-propanol
3. 1-(4-acetamido-2-methoxyphenoxy)-3-[4-(2-chlorophenyl)piperazino]-2-propanol
4. 1-(4-acetamido-2-methoxyphenoxy)-3-[4-(3-fluorophenyl)piperazino]-2-propanol hydrochloride
5. 1-(4-acetamido-2-methoxyphenoxy)-3-[4-(2-fluorophenyl)piperazino]-2-propanol
6. 1-(4-acetamido-2-methoxyphenoxy)-3-[4-(3-trifluoromethylphenyl)piperazino]-2-propanol

Results

The results are shown in the following Table 1.

TABLE 1

| Test Compound Nos. | Dose (mg/kg) | Changes in intracranial pressure (%) Time after administration of test compound (minute) | | | | |
|---|---|---|---|---|---|---|
| | | 0* | 40 | 60 | 120 | 180 |
| 1. | 1.0 | 100 | 81.4 | 85.5 | 91.7 | 92.8 |
| 2. | 1.0 | 100 | 90.5 | 90.7 | 90.1 | 91.5 |
| 3. | 1.0 | 100 | 92.4 | 87.5 | 85.3 | 85.0 |
| | 0.5 | 100 | 84.3 | 80.5 | 86.5 | 86.7 |
| 4. | 1.0 | 100 | 82.6 | 78.1 | 82.2 | 85.2 |
| | 2.0 | 100 | 81.5 | 72.5 | 74.6 | 78.9 |
| 5. | 1.0 | 100 | 84.0 | 84.0 | 81.3 | 87.5 |
| 6. | 1.0 | 100 | 97.0 | 95.0 | 90.5 | 92.8 |
| 20 w/v % mannitol solution (Control) | (8 ml/kg) 1600 | 100 | 74.5 | 77.5 | 90.3 | 95.7 |
| 5 w/v % mannitol solution | (8 ml/kg) 400 | 100 | 105.3 | 105.7 | 108.5 | 107.6 |

Note: *:The intracranial pressure measured before administration of test compound was 70 ± 3.5 mm H₂O (0 minute).

EXAMPLE 2

(Effect of i.v. injection of test compounds on intracranial pressure in rats)

Method

Male SD-strain rats weighing 500 to 800 g (each group consisting of 5 rats) were anesthetized with urethane. 0.03 ml of autologous blood were injected into the brain of the rats to induce an increase in intracranial pressure. The level of increased intracranial pressure in the rats was about twice as high as its initial level 120 to 180 minutes after injection of autologous blood and said increased intracranial pressure was maintained at an approximately same level thereafter. 180 minutes after injection of autologous blood, a solution of a test compound in an aqueous 5 w/v % mannitol solution was infused via the femoral vein of the rats at a rate of 0.2 ml/kg/minute for 40 minutes. Then, the effect of the test compound on the intracranial pressure was calculated according to the following formula:

Changes (%) in intracranial pressure =

$$\frac{\left(\begin{array}{l}\text{Intracranial pressure}\\\text{measured after administration of test compound}\end{array}\right) - \left(\begin{array}{l}\text{Initial intracranial}\\\text{pressure*}\end{array}\right)}{\left(\begin{array}{l}\text{Intracranial pressure}\\\text{measured before administration of test compound**}\end{array}\right) - \left(\begin{array}{l}\text{Initial intracranial}\\\text{pressure*}\end{array}\right)} \times 100$$

Note:
*The initial intracranial pressure, i.e., the normal intracranial pressure measured before injection of autologous blood, was 71.5 ± 3.9 mm H₂O.
**The intracranial pressure measured before administration of test compound was 143 ± 21 mm H₂O.

Test compound

Compound No. 4 listed in Example 1 was used in this experiment.

Results

The results are shown in the following Table 2.

TABLE 2

| Test compound No. | Dose (mg/kg) | Changes in intracranial pressure (%) Time after administration of test compound (minutes) | | | | |
|---|---|---|---|---|---|---|
| | | 0 | 40 | 60 | 120 | 180 |
| 4. | 0.5 | 100 | 68.0 | 65.4 | 74.6 | 76.0 |
| | 1.0 | 100 | 56.7 | 60.9 | 59.2 | 60.6 |
| (Control) 5 w/v % mannitol solution | (8 ml/kg) 400 | 100 | 103.5 | 105.8 | 106.8 | 109.5 |

EXAMPLE 3

(Effect of i.v. injection of test compounds on intracranial pressure in beagle dogs)

Method

Male beagle dogs weighing 10 to 15 kg (each group consisting of 4 beagle dogs) were anesthetized with barbital. A solution of a test compound in an aqueous 5 w/v % mannitol solution was infused via the saphenous vein of the beagle dogs at a rate of 0.1 ml/kg/minute for 40 minutes. Then, the effect of the test compound on the intracranial pressure was estimated in the same manner as described in Example 1.

Test compound

Compound No. 4 listed in Example 1 was used in this experiment.

Results

The results are shown in the following Table 3.

TABLE 3

| Test compound No. | Dose (mg/kg) | Changes in intracranial pressure (%) Time after administration of test compound (minute) | | | | |
|---|---|---|---|---|---|---|
| | | 0* | 40 | 60 | 120 | 180 |
| 4. | 1.0 | 100 | 80.3 | 75.6 | 82.5 | 83.1 |
| 20 w/v % mannitol solution (Control) | (4 ml/kg) 800 | 100 | 75.2 | 80.5 | 103.7 | 110.7 |
| 5 w/v % mannitol | (4 ml/kg) 200 | 100 | 98.5 | 105.2 | 102.5 | 106.7 |

TABLE 3-continued

| Test compound No. | Dose (mg/kg) | Changes in intracranial pressure (%) Time after administration of test compound (minute) | | | | |
|---|---|---|---|---|---|---|
| | | 0* | 40 | 60 | 120 | 180 |
| solution | | | | | | |

Note: *:The intracranial pressure measured before administration of test compound was 110 ± 15 mm H$_2$O (0 minute)

EXAMPLE 4

(Effect of p.o. administration of test compounds on intracranial pressure in rats)

Method

Male SD-strain rats weighing 500 to 800 g (each group consisting of 5 rats) were fasted for about 20 hours, and anesthetized with urethane. A suspension of a test compound in aqueous 0.5 w/v % carboxymethylcellulose was administered orally to the rats. Then, the effect of the compound on the intracranial pressure was estimated in the same manner as described in Example 1.

Test compound

Compound 4 (free base) listed in Example 1 was used in this experiment.

Results

The results are shown in the following Table 4.

TABLE 4

| Test compound | Dose (mg/kg) | Changes in intracranial pressure (%) Time after administration of test compound (minute) | | | | | | |
|---|---|---|---|---|---|---|---|---|
| | | 0* | 20 | 60 | 120 | 180 | 240 | 300 |
| Compound 4 (free base) | 8 | 100 | 85.4 | 83.5 | 77.7 | 76.5 | 75.6 | 77.9 |
| Control 0.5 w/v % CMC solution | (2 ml/kg) | 100 | 108.8 | 115.3 | 112.8 | 113.9 | 131.9 | 153.5 |

Note:
*: The intracranial pressure measured before administration of test compound was 70 ± 3.1 mm H$_2$O (0 minute)

EXAMPLE 5

(Effect of i.v. injection of test compounds on intracranial pressure in rabbits)

Method

Male rabbits weighing 2.8 to 3.2 kg (each group consisting of 6 rabbits) were anethetized with urethane. 0.1 to 0.2 ml of autologous blood were injected into the lateral ventricle of the rabbits to induce a rise in intracranial pressure. The level of intracranial pressure was about 2.3 times as high as its initial level 150 to 180 minutes after injection of autologous blood. 180 minutes after injection of autologous blood, a solution of a test compound in an aqueous 10 w/v % maltose solution was administered intravenously to the rabbits at a rate of 0.1 ml/kg/minute for 20 minutes. Then, the effect of the test compound on the intracranial pressure was calculated in the same manner as described in Example 2. [The initial intracranial pressure (i.e., the normal intracranial pressure measured before injection of autologous blood) was 75±2.6 mm H$_2$O, and the intracranial pressure measured before administration of test compound was 176±16 mm H$_2$O.]

Test compound

Compound 4 listed in Example 1 was used in this experiment.

Results

The results are shown in the following Table 5.

TABLE 5

| Test compound | Dose (mg/kg) | Changes in intracranial pressure (%) Time after administration of test compound (minute) | | | | | | |
|---|---|---|---|---|---|---|---|---|
| | | 0 | 20 | 60 | 120 | 180 | 240 | 300 |
| 4. /0 | 1 | 100 | 96.4 | 91.7 | 82.1 | 94.0 | 91.7 | 91.7 |
| | 2 | 100 | 89.5 | 77.1 | 68.6 | 63.8 | 65.7 | 63.8 |
| w/v % glycerol solution* | (8ml/kg) 800 | 100 | 70.6 | 85.0 | 105.9 | 96.1 | 91.1 | 96.1 |
| | (4ml/kg) 400 | 100 | 71.2 | 91.2 | 112.5 | 126.5 | 127.2 | 122.5 |
| (Control) | (4ml/kg) | | | | | | | |
| 10 w/v % maltose solution | 400 | 100 | 109.9 | 120.9 | 121.5 | 123.1 | 140.7 | 152.7 |

Note:
*:An aqueous solution containing 10 w/v % of glycerol, 5 w/v % of fructose and 0.9 w/v % of sodium chloride

EXAMPLE 6

(Effect of test compounds on common carotid blood flow in cats)

Method

Cats weighing 2.5 to 3.5 kg (each group consisting of 5 cats) were anesthetized with urethane and chloralose. A solution of a test compound in an aqueous 10 w/v % maltose solution was injected into the right thyroid artery of the cats. The common carotid artery blood flow was continuously monitored via the flow probe set at the common carotid artery. The flow probe was connected to an electromagnetic flow meter, and recordings were made on graph paper. The effect of the test compound on the common carotid blood flow was estimated 30 seconds after administration of the test compound.

Test compound

Compound No. 4 listed in Example 1 was used in this experiment.

Results

The results are shown in the following Table 6.

TABLE 6

| Test compound No. | Dose (μg/kg) | Increase in common carotid blood flow (Δml/minute)* |
|---|---|---|
| 4 | 1 | 3.5 ± 0.8 |
| | 5 | 6.1 ± 0.6 |
| | 10 | 8.8 ± 1.3 |
| | 10 | 2.6 ± 0.2 |
| Papaverine | 25 | 5.4 ± 0.6 |

Note:
:The common carotid blood flow measured before administration of test compound was 24.1 ± 0.9 ml/minute.

EXAMPLE 7

(Acute toxicity)

Method

A test compound was administered orally or intravenously to male ddY-strain mice weighing 21 to 25 g (each group consisting of 10 mice), and the mice were observed for a week after administration of the test compound. The 50% lethal dose ($LD_{50}$) of the test compound was calculated according to the Weil's method from the number of mice died a week after the administration.

Results

The results are shown in the following Table 7.

TABLE 7

| Test compounds | $LD_{50}$ |
|---|---|
| 1-(4-acetamido-2-methoxyphenoxy)-3-[4-(3-fluorophenyl)piperazino]-2-propanol (free base) | 1550 mg/kg (p.o.) |
| 1-(4-acetamido-2-methoxyphenoxy)-3-[4-(3-fluorophenyl)piperazino]-2-propanol hydrochloride | 280 mg/kg (i.v.) |

EXAMPLE 8

(Subacute toxicity)

Method 1-(4-acetamido-2-methoxyphenoxy)-3-[4-(3-fluorophenyl)-piperazino]-2-propanol hydrochloride was administered intraperitoneally to male and female Wistar-KBL-strain rats weighing 180 to 200 g (each group consisting of 10 male rats and 10 female rats) at a dose of 10, 30 or 100 mg/kg once a day for 30 consecutive days. In each of these doses, all rats survived at least for 30 days after the administration of the test compound was commenced.

EXAMPLE 9

(Intramuscular injection)

4 g of 1-(4-acetamido-2-methoxyphenoxy)-3-[4-(3-fluorophenyl)piperazino]-2-propanol hydrochloride and 50 g of sorbitol were dissolved in about 900 ml of distilled water, and the solution was adjusted to a total volume of one liter with distilled water. The solution was filtered through a membrane filter (pore size: 0.22 μm), and the filtrate was filled into ampoules (1.1 ml per ampoule). The ampoules were sealed and then sterilized for 60 minutes with steam (100° C.)

EXAMPLE 10

(Intravenous injection)

Citric acid was dissolved in distilled water to give an aqueous 0.003 N citric acid solution. 0.4 g of 1-(4-acetamido-2-methoxyphenoxy)-3-[4-(3-fluorophenyl)-piperazino[-2-propanol and 9 g of sodium chloride were dissolved in about 900 ml of the aqueous citric acid solution. The solution thus obtained was adjusted to a pH of 6 to 6.5 with an aqueous 0.1 N sodium hydroxide solution, and then adjusted to a total volume of one liter with distilled water. Then, the solution was filtered by a membrane filter (pore size: 0.22 μm), and the filtrate was filled into ampules (5.3 ml per ampule). The ampules were sealed and then sterilized for 60 minutes with steam (100° C.).

EXAMPLE 11

(Intravenous drip infusion solution)

0.1 g of 1-(4-acetamido-2-methoxyphenoxy)-3-[4-(3-fluorophenyl)piperazino]-2-propanol hydrochloride and 50 g of mannitol were dissolved in about 900 ml of distilled water. The solution was adjusted to a pH of 6.5 to 7.0 with an aqueous 0.1 N sodium hydroxide solution, and then adjusted to a total volume of one liter with distilled water. The solution thus obtained was filtered through a membrane filter (pore size: 0.22 μm), and the filtrate was filled into vials (206 ml per vial). The vials were sealed and then sterilized at 115° C. for 30 minutes in an autoclave.

EXAMPLE 12

(Intravenous drip infusion solution)

An intravenous drip infusion solution was prepared in the same manner as described in Example 11 except that 50 g of xylitol were used instead of 50 g of mannitol.

EXAMPLE 13

(Intravenous drip infusion solution)

An intravenous drip infusion solution was prepared in the same manner as described in Example 11 except that 50 g of fructose were used instead of 50 g of mannitol.

EXAMPLE 14

(Intravenous drip infusion solution)

An intravenous drip infusion solution was prepared in the same manner as described in Example 11 except that 25 g of glycerol and 50 g of sorbitol were used instead of 50 g of mannitol.

EXAMPLE 15

(Tablets)

| | |
|---|---|
| 1-(4-acetamido-2-methoxyphenoxy)-3-[4-(3-fluorophenoxy)-piperazinol]-2-propanol | 25 g |
| lactose | 60 g |
| corn starch | 41 g |

The mixture of these ingredients was granulated with the aid of 3 g of hydroxypropylcellulose (a binding agent). One g of magnesium stearate was added to the resultant granules, and the mixture was then compressed into tablets (7.5 mm in diameter, weight: 130 mg).

EXAMPLE 16

(Powder)

| | |
|---|---|
| 1-(4-acetamido-2-methoxyphenoxy)-3-[4-(3-fluorophenoxy)piperazino]-2-propanol | 100 g |
| corn starch | 900 g |

The mixture of these ingredients was thoroughly mixed and the mixture was passed through a standard sieve (350μ aperture) to give powders containing 10 w/v % of said propanol.

EXAMPLE 17

(Capsules)

| | |
|---|---|
| 1-(4-acetamido-2-methoxyphenoxy)-3-[4-(3-fluorophenoxy)piperazino)]-2-propanol | 25 g |
| lactose | 100 g |
| corn starch | 44 g |
| crystalline cellulose | 60 g |
| magnesium stearate | 1 g |

The above-mentioned ingredients were thoroughly mixed and the mixture was encapsulated to give capsules containing 230 mg of said mixture per each capsules.

Preparation of the propanol derivative (I)

(1) 1.0 g of 3-(4-acetamido-2-methoxyphenoxy)-1,2-epoxypropane is dissolved in 40 ml of ethanol, and 750 mg of 4-phenylpiperazine are added thereto. The mixture is stirred at room temperature for 18 hours. Then, the mixture is concentrated under reduced pressure to remove ethanol. The residue is recrystallized from a mixture of ethyl acetate and methanol, whereby 1.55 g of 1-(4-acetamido-2-methoxyphenoxy)-3-(4-phenyl-piperazino)-2-propanol are obtained as colorless needles. M.p. 154°–156° C.

Hydrochloride: M.p. 242°–244° C. (decomp.)
Methanesulfonate: M.p. 191°–193° C.

(2) 800 mg of 3-(4-acetamido-2-methoxyphenoxy)-1,2-epoxypropane are dissolved in 40 ml of ethanol, and 670 mg of 4-(2-fluorophenyl)piperazine are added thereto. The mixture is refluxed for 4 hours. Then, the mixture is concentrated under reduced pressure to remove ethanol. The residue is recrystallized from a mixture of isopropyl alcohol and isopropyl ether, whereby 770 mg of 1-(4-acetamido-4-methoxyphenoxy)-3-[4-(2-fluorophenyl)piperazino]-2-propanol are obtained as colorless granules.

The mother liquor obtained after recrystallization is concentrated to dryness. The residue is purified by silica gel chromatography (Solvent: 2% ethanol-chloroform), and then recrystallized from a mixture of isopropyl alcohol and isopropyl ether. 460 mg of 1-(4-acetamido-2-methoxyphenoxy)-3-[4-(2-fluorophenyl)piperazino]-2-propanol are further obtained. M.p. 143.5°–144.5° C.

The following compounds are obtained in the same manner as described in paragraph (1) or (2)

1-(4-acetamido-2-methoxyphenoxy)-3-[4-(2-methyl-phenyl)-piperazino]-2-propanol, M.p. 126.5°–128° C.

1-(4-acetamido-2-methoxyphenoxy)-3-[4-(4-chloro-phenyl)-piperazino]-2-propanol, M.p. 177°–178.5° C.

1-(4-acetamido-2-methoxyphenoxy)-3-[4-(3-chloro-phenyl)-piperazino]-2-propanol, M.p. 141°–143.5° C.

1-(4-acetamido-2-methoxyphenoxy)-3-[4-(2-chloro-phenyl)-piperazino]-2-propanol, M.p. 137.5°–140° C.

1-(4-acetamido-2-methoxyphenoxy)-3-[4-(4-fluoro-phenyl)-piperazino]-2-propanol, M.p. 175.5°–176.5° C.

1-(4-acetamido-2-methoxyphenoxy)-3-[4-(3-fluoro-phenyl)-piperazino]-2-propanol, M.p. 144.5°–146° C.

Hydrochloride: M.p. 224°–226° C.
1-(4-acetamido-2-methoxyphenoxy)-3-[4-(3-tri-fluoromethylphenyl)piperazino]-2-propanol, M.p. 125°–127° C.

What we claim is:

1. A method of reducing increased intracranial pressure in a warm-blooded animal which comprises administering to a warm-blooded animal in need of such reduction of intracranial pressure an intercranial pressure reducing amount of the propanol derivative of the formula:

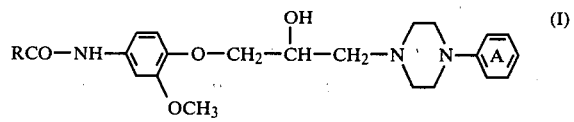

wherein R is alkyl having one to 4 carbon atoms and Ring A is phenyl, halogenophenyl, methylphenyl or trifluoromethylphenyl, or a pharmaceutically acceptable acid addition salt thereof.

2. The method of claim 1 wherein Ring A is phenyl, chlorophenyl, fluorophenyl, methylphenyl, or trifluoromethylphenyl.

3. The method according to claim 2, wherein the propanol derivative (I) or a pharmaceutically acceptable acid addition salt thereof is administered at a daily dose of 0.05 to 50 mg (in terms of free base) per kilogram of body weight.

4. The method according to claim 2, wherein the propanol derivative (I) or a pharmaceutically acceptable acid addition salt thereof is administered orally at a daily dose of 1 to 10 mg (in terms of free base) per kilogram of body weight.

5. The method according to claim 2, wherein the propanol derivative (I) of a pharmaceutically acceptable acid addition salt thereof is administered parenterally at a daily dose of 0.1 to 5 mg (in terms of free base) per kilogram of body weight.

6. The method according to claim 2, 3, 4 or 5, wherein the propanol derivative (I) is selected from the group consisting of 1-(4-acetamido-2-methoxyphenoxy)-3-(4-phenylpiperazino)-2-propanol, 1-(4-acetamido-2-methoxyphenoxy)-3-[4-(chlorophenyl)-piperazino]-2-propanol and 1-(4-acetamido-2-methoxyphenoxy)-3-[4-(fluorophenyl)piperazino]-2-propanol.

7. The method according to claim 2, 3, 4 or 5, wherein the propanol derivative (I) is selected from the group consisting of 1-(4-acetamido-2-methoxyphenoxy)-3-(4-phenylpiperazino)-2-propanol, 1-(4-acetamino-2-methoxyphenoxy)-3-[4-(2-chlorophenyl)-piperazino]-2-propanol, 1-(4-acetamido-2-methoxyphenoxy)-3-[4-(2-fluorophenyl)piperazino]-2-propanol and 1-(4-acetamido-2-methoxyphenoxy)-3-[4-(3-fluorophenyl)-piperazino]-2-propanol.

8. The method according to claim 7, wherein the propanol derivative (I) is 1-(4-acetamido-2-methoxyphenoxy)-3-(4-phenylpiperadino)-2-propanol.

9. The method according to claim 7, wherein the propanol derivative (I) is 1-(4-acetamido-2-methoxyphenoxy)-3-[4-(2-chlorophenyl)piperazino]-2-propanol.

10. The method according to claim 7, wherein the propanol derivative (I) is 1-(4-acetamido-2-methoxyphenoxy)-3-[4-(3-fluorophenyl)piperazino]-2-propanol.

11. The method according to claim 7, wherein the propanol derivative (I) is 1-(4-acetamido-2-methoxyphenoxy)-3-[4-(2-fluorophenyl)piperazino]-2-propanol.

* * * * *